US012557817B2

(12) United States Patent
　　Choi et al.

(10) Patent No.:　US 12,557,817 B2
(45) Date of Patent:　Feb. 24, 2026

(54) BIOACTIVE PEPTIDES HAVING DETRIMENTAL EFFECTS ON PEST SLUGS

(71) Applicants: The United States of America, as represented by the Secretary of Agriculture, Washington, DC (US); OREGON STATE UNIVERSITY, Corvallis, OR (US)

(72) Inventors: Man Y. Choi, Albany, OR (US); Ruth C. Martin, Corvallis, OR (US); Seungjoon Ahn, Corvallis, OR (US); Rory Mc Donnell, Corvallis, OR (US); Sujaya Rao, Roseville, MN (US)

(73) Assignees: The United States of America, as represented by the Secretary of Agriculture, Washington, DC (US); Oregon State University, Corvallis, OR (US)

( * ) Notice: Subject to any disclaimer, the term of this patent is extended or adjusted under 35 U.S.C. 154(b) by 49 days.

(21) Appl. No.: 18/331,667

(22) Filed: Jun. 8, 2023

(65) Prior Publication Data

US 2023/0309566 A1　　Oct. 5, 2023

Related U.S. Application Data

(62) Division of application No. 17/002,390, filed on Aug. 25, 2020, now Pat. No. 11,723,370.

(60) Provisional application No. 62/892,605, filed on Aug. 28, 2019.

(51) Int. Cl.
| | |
|---|---|
| *A01N 63/50* | (2020.01) |
| *A01M 1/20* | (2006.01) |
| *C07K 7/06* | (2006.01) |
| *C07K 7/08* | (2006.01) |
| *C07K 14/00* | (2006.01) |

(52) U.S. Cl.
CPC ........... *A01N 63/50* (2020.01); *A01M 1/2011* (2013.01); *C07K 7/06* (2013.01); *C07K 7/08* (2013.01); *C07K 14/001* (2013.01)

(58) Field of Classification Search
None
See application file for complete search history.

(56) References Cited

PUBLICATIONS

Proekt et al. "Identification of a New Neuropeptide Precursor Reveals a Novel Source of Extrinsic Modulation in the Feeding System of Aplysia" The Journal of Neuroscience 25:9637-9648. (Year: 2005).*
GenBank KAG0657294.1 (Year: 2021).*
GenBank MDT8376302.1 (Year: 2023).*
GenBank NLV39710.1 (Year: 2020).*
GenBank MBN1675911.1 (Year: 2021).*
NCBI Reference Sequence WP_367429143.1 (Year: 2024).*
Seung-Joon Ahn et al., Scientific Reports, Identification and functional characterization of the first molluscan neuromedin U receptor in the slug, Deroceras reticulatum, 2020, pp. 1-13.
Alex Proekt et al., The Journal of Neuroscience, Identification of a New Neuropeptide Precursor Reveals a Novel Source of Extrinsic Modulation in the Feeding System of Aplysia, Oct. 19, 2005 • 25(42):9637-9648.
GenBank ARS01385.1. "myomodulin 3, partial [Deroceras reticulatum]". (Year: 2017).

* cited by examiner

*Primary Examiner* — Sudhakar Katakam
*Assistant Examiner* — Zachary J Miknis
(74) *Attorney, Agent, or Firm* — John Fado; Mark McNemar

(57) ABSTRACT

Provided herein are synthetic peptides developed from slug and insect neuropeptides. Peptides described can be used to repel, control or deter slugs, including the gray garden slug (*Deroceras reticulatum*), from feeding on agricultural and horticultural plants. The peptides can be combined with bait materials, or applied directly to plants or areas, or produced by genetically modified plants.

20 Claims, 9 Drawing Sheets

Specification includes a Sequence Listing.

FIG. 2A                                    FIG. 2B

BIOACTIVE PEPTIDES HAVING DETRIMENTAL EFFECTS ON PEST SLUGS

CROSS-REFERENCE

The present application claims priority to U.S. Provisional Patent Application Ser. No. 62/892,605 filed Aug. 28, 2019, and U.S. patent application Ser. No. 17/002,390 filed Aug. 25, 2020, the contents of which are expressly incorporated herein by reference.

SEQUENCE LISTING

The instant application contains a Sequence Listing XML required by 37 C.F.R. § 1.831(a) which has been submitted in XML file format via the USPTO patent electronic filing system and is hereby incorporated by reference in its entirety. The XML file was created on Jun. 6, 2023, is named Sequence_Listing-005523.xml, and has 34.2 KB bytes.

BACKGROUND OF THE INVENTION

Field of Invention

Provided herein are synthetic peptides developed from slug and insect neuropeptides. Peptides described can be used to repel, control or deter slugs, including the gray garden slug (*Deroceras reticulatum*), from feeding on agricultural and horticultural plants. The peptides can be combined with bait materials, or applied directly to plants or areas.

Background

The gray garden slug, or gray field slug, *Deroceras reticulatum*, is native to Europe, omnivorous, and is the most destructive pest on a variety of crops in greenhouses and fields. Infestations and the resulting damage/problems associated with slugs are increasing worldwide. Slugs affect a wide range of cropping systems including seed production, field crops, row crops, Christmas tree farms, and horticultural nurseries. In Oregon alone, in new fields, the cost of bait applications, direct loss of plants, and the cost of replanting is estimated to cost the seed industry >$50 million annually. In established grass seed fields, slug bait applications are estimated at ~$7 million annually, with an additional $38 million in losses from crop damage. Globally, those economic impacts are increasing every year.

Currently, major control methods for slugs rely on conventional pesticides. Multiple applications of sprays, baits or granules are used regardless of the level of residues accumulating in a field. Unfortunately, some of these chemicals are non-specific, and kill non-target and beneficial organisms such as earthworms in the soil. Additionally, this strategy is costly and inefficient at suppressing slugs to a level below a certain economical threshold because appropriate soil moisture and weather conditions are necessary for effective delivery of the chemical and consequent slug control in the field. Another risk of chemical applications is the potential for developing chemical resistance in slugs (Salmijah et al, Plant Prot. Quart., (2000) 15:2-5. As presented herein, we have developed novel peptides that are commercially viable and specific for slugs.

SUMMARY OF THE INVENTION

In one embodiment, the present disclosure provides a synthetic peptide having SEQ ID NO: 17, SEQ ID NO: 18, SEQ ID NO: 3, SEQ ID NO: 4, or a combination thereof. Such compositions can include any one of these sequences specifically, namely, SEQ ID NO: 18, SEQ ID NO: 17, SEQ ID NO: 3, or SEQ ID NO: 4.

Another embodiment provided herein is a molluscicide for controlling a slug, the composition comprising an effective amount of a synthetic peptide having SEQ ID NO: 17, SEQ ID NO: 18, SEQ ID NO: 3, SEQ ID NO: 4, or a combination thereof. Such compositions can include any one of these sequences specifically, namely, SEQ ID NO: 18, SEQ ID NO: 17, SEQ ID NO: 3, or SEQ ID NO: 4. In some embodiments, the molluscicide also has an agriculturally acceptable carrier. In other embodiments, molluscicides disclosed herein can also have a preservative, a dispersant, a fungicide, an herbicide, an attractant, a phagostimulant, a bait material, or a combination thereof.

Another embodiment disclosed herein is a bait composition for controlling a slug, comprising: an effective amount of a synthetic peptide having SEQ ID NO: 17, SEQ ID NO: 18, SEQ ID NO: 3, SEQ ID NO: 4, or a combination thereof; a food material; and optionally a phagostimulant.

The present disclosure further provides a method for controlling a slug comprising contacting a slug or its environment with a biologically effective amount of a synthetic peptide or molluscicide, wherein the mortality of said slug increases. In specific embodiments, the slug is *Deroceras reticulatum*.

An additional embodiment disclosed herein is a composition comprising a synthetic peptide having SEQ ID NO: 19, SEQ ID NO: 20, SEQ ID NO: 21, SEQ ID NO: 22, SEQ ID NO: 26, SEQ ID NO: 27, SEQ ID NO: 28, or a combination thereof.

Also provided herein is a molluscicide composition for controlling a slug, the composition comprising an effective amount of a synthetic peptide having SEQ ID NO: 19, SEQ ID NO: 20, SEQ ID NO: 21, SEQ ID NO: 22, SEQ ID NO: 26, SEQ ID NO: 27, SEQ ID NO: 28, or a combination thereof.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

FIG. 6 provides a graphic representation of phenotypic effects of injection of molluscicidal peptides. Mortality of slugs injected with SEQ ID NO: 1, SEQ ID NO: 3, SEQ ID NO: 19, SEQ ID NO: 25, or SEQ ID NO: 26 within 24 h under dry conditions (Petri dish) is shown.

FIG. 7 provides a graphic representation of phenotypic effects of injection of molluscicidal peptides. Mortality of slugs injected with SEQ ID NO: 3, SEQ ID NO: 19, SEQ ID NO: 25 or SEQ ID NO: 26 within 24 h under wet conditions (Petri dish with wet paper towel) is shown.

DETAILED DESCRIPTION OF THE INVENTION

Figure 1:
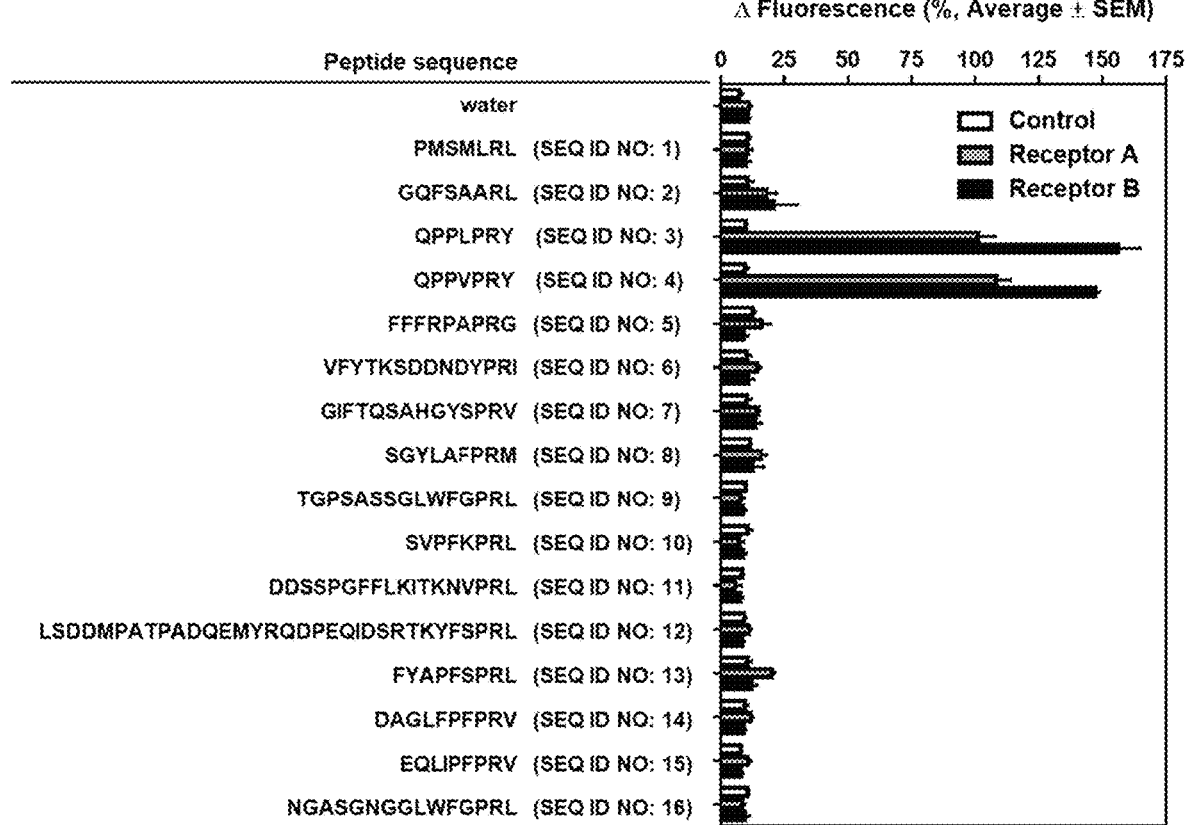
FIG. 1 provides a graphic representation of peptide ligand screening results. Peptides described herein (Table 1) produced fluorescence signals when exposed to recombinant Sf9 cells expressing receptor variant A or variant B. Unmodified Sf9 cells were tested as a negative control.

Neuropeptides are part of a large group of neurohormones that have important regulatory functions and are found in invertebrates. A variety of peptide families from Mollusca have been identified and classified by their core structures and functionalities. These neuropeptide ligands bind to G Protein-coupled receptors (GPCRs), a large group of signaling receptors for various signal transductions. GPCRs are membrane embedded proteins, also known as 7 transmembrane receptors, activated by a wide variety of stimulants including light, odorant molecules, peptide and non-peptide neurotransmitters, hormones, growth factors and lipids. They control a wide variety of physiological processes including sensory transduction, cell-cell communication, neuronal transmission, and hormonal signaling.

The PRXamide (X=any amino acid) family of neuropeptides is based on the core amino acid sequence at the C-terminal end that are required for activity and on sequence homology of their GPCRs (Jurenka, R., Adv. Insect Physiol., (2015) 49: 123-70). The PRXamide family of neuropeptides are ubiquitous in invertebrate animals. The family includes proteins such as pyrokinin, pheromone biosynthesis-activating neuropeptide, diapause hormone, CAPA/periviscerokinin (a.k.a. cardioacceleratory peptide 2b), and ecdysis triggering hormone in many arthropods and gastropods. However, knowledge about structure of specific peptide ligands and their receptors is necessary to more fully understand their interactions to facilitate the development of antagonists and agonists.

Disclosed herein are specific synthetic peptides that target slug GPCRs, interfering with normal functioning and leading to detrimental effects. In specific embodiments, the peptides (SEQ ID NO: 3; SEQ ID NO: 4; SEQ ID NO: 19; SEQ ID NO: 25; SEQ ID NO: 26) provided a novel approach for bio-control of these important agricultural and horticultural pests.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", $2^{nd}$ ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

"Activity" of a synthetic peptide, as used herein, refers to the capacity to obtain mortality or paralysis in slugs when such slugs are exposed to the peptides (e.g., via feeding or injection), which mortality or paralysis is significantly higher than a negative control (e.g., a buffer).

"Carrier" as used herein refers to any method of dispersal, dispensation, application, timed-release, encapsulation, microencapsulation, or the like to apply the slug-affecting composition as further described herein. In embodiments, such "carriers" may include a variety of microencapsulation, controlled-release, and other dispersion technologies available to those of ordinary skill in the art.

"Control" or "controlling" as used herein refers to any means for preventing infestation, reducing the population of already infested areas, or elimination of pest population(s) whose "control" is desired. Indeed, "controlling" as used herein refers to any indicia of success in prevention, elimination, reduction, repulsion, or amelioration of a pest population or pest problem.

An "effective amount" is an amount sufficient to effect desired beneficial or deleterious results. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The terms "polypeptide, peptide or protein" refer to polymers in which the monomers are amino acid residues which are joined together through amide bonds. When the amino acids are alpha-amino acids, either the L-optical isomer or the D-optical isomer can be used. The terms are used interchangeably herein. These terms apply to amino acid polymers in which one or more amino acid residues are an artificial chemical mimetic of a corresponding naturally occurring amino acid, as well as to naturally occurring amino acid polymers and non-naturally occurring amino acid polymers.

A "conservative substitution" in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamine or aspartate; or (d) a residue having a bulky side chain, for example, phenylalanine, is substituted for (or by) one not having a side chain, for example, glycine.

The term "phagostimulant" refers to any substance that will entice the slug to ingest the selected bioactive peptide. Suitable phagostimulants include but are not limited to syrups, honey, aqueous solutions of sucrose, artificial sweeteners such as sucralose, saccharin, and other artificial sweeteners, starch, amino acids, and other proteins. Additionally, the bait material containing the bioactive peptide disclosed herein would be incorporated in water soluble baits, oil-in water or oil/water emulsion baits, liquid type or gel type of baits.

The ready-to-use preparations of phagostimulants can be in the form of a wettable powder, flowable concentrate solution, water soluble granules, ultra-low volume formulation, and the like, which can be applied to the target habitat. Phagostimulants can be used in combination with peptides of the present disclosure to enhance or encourage uptake by target pests. In essence, the combination is a slug bait. Such baits can also include any other component desired by one of skill in the art, such as carriers, preservatives, odorants, molluscicides, insecticides and the like. Phagostimulants can include carbohydrates such as glucose, fructose, arabinose, sorbitol, maltose, glucose, lactose, or any other small sugar. It will be obvious to a person skilled in the art that some carbohydrates and/or amino acids are likely to act as a deterrent. Thus, a bait, or other composition of the present invention can include phagostimulant(s) that attract a target slug and components that repel other animals (such as beneficial insects, pets and wildlife). Such variations are easily appreciated by any person skilled in the art.

The "sequence identity" of two related nucleotide or amino acid sequences, expressed as a percentage, refers to the number of positions in the two optimally aligned sequences which have identical residues ($\times 100$) divided by the number of positions compared. A gap, i.e., a position in an alignment where a residue is present in one sequence but not in the other is regarded as a position with non-identical residues. The alignment of the two sequences is performed by the Needleman-Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

Peptides

The peptides provided herein can be synthesized by any suitable method, such as exclusively solid-phase techniques, partial solid-phase techniques, fragment condensation, or classical solution addition. The amino acids of the compounds of the invention are typically joined to adjacent groups through amide linkages. For example, without being limited thereto, the peptide variants may be synthesized by methods well known to those skilled in the art of peptide synthesis, e.g., solution phase synthesis [see Finn and Hoffman, In "Proteins," Vol. 2, 3rd Ed., H. Neurath and R. L. Hill (eds.), Academic Press, New York, pp. 105-253 (1976)], or solid phase synthesis [see Barany and Merrifield, In "The Peptides," Vol. 2, E. Gross and J. Meienhofer (eds.), Academic Press, New York, pp. 3-284 (1979)], or stepwise solid phase synthesis as reported by Merrifield [J. Am. Chem. Soc. 85: 2149-2154 (1963)], the contents of each of which are incorporated herein by reference. However, the peptide fragments are preferably produced by recombinant DNA techniques, which are particularly suitable for large-scale use.

Synthesis by the use of recombinant DNA techniques, for the purpose of this application, should be understood to include the suitable employment of structural genes coding for the sequence as specified hereinafter. The synthetic peptides may also be obtained by transforming a microorganism or plant using an expression vector including a promoter or operator, or both, together with such structural genes and causing such transformed microorganisms or plant to express the peptide.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Sambrook et al. [Molecular Cloning: A Laboratory Manual, Cold Springs Harbor Laboratory, 1989] or Ausubel et al. [Current Protocols in Molecular Biology, John Wiley & Sons, Inc, 1995], the contents of each of which are herein incorporated by reference. Further, the vectors may be non-fusion vectors (i.e., those producing the peptides of the invention not fused to any heterologous polypeptide), or alternatively, fusion vectors (i.e., those producing the peptides fused to a vector encoded polypeptide). The fusion proteins would of course vary with the particular vector chosen.

TABLE 1

| Synthetic peptide sequences | | |
|---|---|---|
| Sequence | Source | SEQ ID NO: |
| PMSMLRL | *D. reticulatum* | SEQ ID NO: 1 |
| GQFSAARL | *D. reticulatum* | SEQ ID NO: 2 |
| QPPLPRY | *D. reticulatum* | SEQ ID NO: 3 |
| QPPVPRY | *D. reticulatum* | SEQ ID NO: 4 |
| FFFRPAPRG | *D. reticulatum* | SEQ ID NO: 5 |
| VFYTKSDDNDYPRI | *D. reticulatum* | SEQ ID NO: 6 |
| GIFTQSAHGYSPRV | *D. reticulatum* | SEQ ID NO: 7 |
| SGYLAFPRM | *D. reticulatum* | SEQ ID NO: 8 |
| TGPSASSGLWFGPRL | *D. melanogatser* | SEQ ID NO: 9 |
| SVPFKPRL | *D. melanogatser* | SEQ ID NO: 10 |
| DDSSPGFFLKITKNVPRL | *D. melanogatser* | SEQ ID NO: 11 |
| LSDDMPATPADQEMYRQDPEQIDSRTKYFSPRL | *H. zea* | SEQ ID NO: 12 |
| FYAPFSPRL | *H. halys* | SEQ ID NO: 13 |
| DAGLFPFPRV | *H. halys* | SEQ ID NO: 14 |
| EQLIPFPRV | *H. halys* | SEQ ID NO: 15 |
| NGASGNGGLWFGPRL | *H. halys* | SEQ ID NO: 16 |
| QPPXPRY | generic formula | SEQ ID NO: 17 |
| XXXXPRY | generic formula | SEQ ID NO: 18 |
| APPLPRY | Synthetic | SEQ ID NO: 19 |
| QAPLPRY | Synthetic | SEQ ID NO: 20 |
| QPALPRY | Synthetic | SEQ ID NO: 21 |
| QPPAPRY | Synthetic | SEQ ID NO: 22 |
| QPPLARY | Synthetic | SEQ ID NO: 23 |
| QPPLPAY | Synthetic | SEQ ID NO: 24 |
| QPPLPRA | Synthetic | SEQ ID NO: 25 |
| LPRY | Synthetic | SEQ ID NO: 26 |
| PPLPRY | Synthetic | SEQ ID NO: 27 |
| PLPRY | Synthetic | SEQ ID NO: 28 |

Peptide Compositions

In particular embodiments, the present invention provides a composition having synthetic peptide represented by one or more of SEQ ID NOs: 1-28 (Table 1). The synthetic peptides were developed based on sequences from *Deroceras reticulatum* (gray garden slug) and various insects (*Drosophila melanogaster, Helicoverpa zea*, and *Halyomorpha halys*). In specific embodiments, compositions containing peptides having SEQ ID NO: 3, SEQ ID NO: 4, SEQ ID NO: 19, SEQ ID NO: 20, SEQ ID NO: 21, SEQ ID NO: 22, SEQ ID NO: 27, SEQ ID NO: 28, or a combination of two or more of these peptides is provided. Peptides utilized herein, can be any one within the generic formulas provided (SEQ ID NO: 17, SEQ ID NO: 18). Typically, peptides of the present disclosure are provided to a target recipient (e.g., slug) in an amount sufficient to induce a detrimental effect (e.g., death). Peptides of the present disclosure can be in the amide form—having an ($NH_2$) group at the C-terminus.

Typically, a peptide or peptide mixture of the present invention is provided to a target pest in an amount sufficient to cause a detrimental effect (e.g., paralysis or death) to a mollusk, such as a slug or snail. For example, when a slug is feeding on peptide-laden plant material (e.g., leaf), the slug ingests a sufficient level of peptide to result in a detrimental effect. In some embodiments, a combination of two or more peptides (e.g., a combination of SEQ ID NO: 3 and SEQ ID NO: 4) can be combined in a single treatment, on a single plant, or applied to a target area. Where two or more peptides are utilized, they can be provided in a single application, or in multiple, sequentially applied applications.

In addition, the peptide(s) of the present invention, compositions of the present invention that are intended to be applied to a plant, or an area, can also comprise one or more chemoattractants, phagostimulants, visual attractants, insecticides, pheromones, fungicides, or combinations thereof. Such additional components are well known in the art and are readily chosen to complement compositions of the present invention, but are not specifically integral to the present invention. These additional components can be formulated to be coated on a plant, plant part, leaf, fruit, vegetable, stem or other plant structure. In certain aspects the additional component(s) are combined with one or more excipients, buffering agents, carriers, etc. that are also well known in the art.

In some embodiments of the present disclosure, one or more peptides provided herein are expressed in a transgenic plant, such that ingestion of the transgenic plant tissues by a target pest leads to the effect. Methods of producing transgenic plants are well known in the art.

Application to Target Plants

Compositions of the inventions disclosed herein can be applied to soil, fruits, vegetables, crops, and any other desired target using any delivery methodology known to those of skill in the art. For example, peptide-containing compositions can be applied to the desired locale via methods and forms including, but not limited to, sprays, granules, flood/furrow methods, sprinklers, fumigation and drip irrigation. In embodiments of the disclosure where the compositions are sprayed onto a desired locale, the compositions can be delivered as a liquid suspension, emulsion, microemulsion or powder. In other embodiments, granules or microcapsules can be used to deliver the compositions of the disclosure.

The compositions of the present disclosure can be applied to plants and/or crops by any convenient method, for example, by using a fixed application system such as a center pivot irrigation system. Application to fields of plants and/or crops is made by air spraying, i.e., from an airplane or helicopter, or by land spraying. For example, land spraying may be carried out by using a high flotation applicator equipped with a boom, by a back-pack sprayer or by nurse trucks or tanks. One of skill in the art will recognize that these application methodologies are provided by way of example and that any applicable methods known in the art or developed in the future can be utilized.

Having generally described this invention, the same will be better understood by reference to certain specific examples, which are included herein to further illustrate the invention and are not intended to limit the scope of the invention as defined by the claims.

EXAMPLES

Example 1

Slugs

The gray garden slugs utilized herein (*Deroceras reticulatum*) were collected in Corvallis, Oregon, USA, and maintained with carrot and lettuce in a controlled incubator (13° C., 90% RH, 14: 10=light:dark, dim light).

RNA Isolation and cDNA Synthesis

Mature slugs were individually homogenized after removing the surface slime in lysis buffer (PURELINK RNA Mini Kit—Invitrogen, Thermo Fisher Scientific, Waltham, MA, USA) using a PYREX® glass pestle tissue grinder (Corning, Corning, NY, USA). Total RNA was isolated using the PURELINK RNA Mini Kit according to manufacturer's instructions. The total RNA was quantified by NanoDrop 2000 spectrophotometer (Thermo Fisher Scientific) and stored at −80° C. until use. For 5'- and 3'-rapid amplification of cDNA ends (RACEs)-PCR, 5'- and 3'-RACE-ready cDNAs were synthesized with 1 µg of total RNA using SMARTer® RACE 5'/3' Kit (Clontech Laboratories, Takara, Mountain View, CA, USA). The first-strand cDNA was synthesized with 1 µg of total RNA using a SuperScript IV First-Strand Synthesis System (Invitrogen). cDNAs were stored at −20° C. until use.

Molecular Cloning of the Slug Receptor A and B

Both 5'- and 3'-RACEs of the partial transcript sequences obtained from the slug transcriptome were amplified using Phusion High Fidelity DNA Polymerase (Thermo Fisher Scientific) under the following PCR conditions: 98° C. for 30 s, 35 cycles of 98° C. for 10 s, 68° C. for 20 s, and 72° C. for 1 min, then 72° C. for 10 min using a Veriti 96 Fast Thermal Cycler (Applied Biosystems, Foster City, CA, USA). Using a pair of gene-specific primers, target sequences were amplified from the first-strand cDNA using Phusion High Fidelity DNA polymerase under the following PCR conditions: 98° C. for 30 s, 35 cycles of 98° C. for 10 s, 55° C. for 20 s, and 72° C. for 1 min, then 72° C. for 10 min using Veriti 96 Fast Thermal Cycler. PCR products were run in 1.2% agarose gel, purified and cloned into pJET1.2 vector (Thermo Fisher Scientific) for sequencing. The sequencing results were analyzed using Geneious 8.1 software (Biomatters, Newark, NJ, USA).

Functional Expression of the Slug Receptor A and B

The open reading frames (ORFs) of *D. reticulatum* GPCRs were inserted into a pIB/V5-His TOPO® TA expression vector (Thermo Fisher Scientific) to be expressed in Sf9 cells as described previously (Choi et al., Gen. Comp. Endocrinol., (2017) 246:354-62). To add a Kozak sequence (G/ANN<u>ATG</u>G) in the translation initiation the ORFs of *D. reticulatum* GPCRs were amplified using specific primer sets. The sequences of two different ORFs of *D. reticulatum* GPCRs were confirmed after insertion into the expression vector.

Binding Assay with Peptides

Small synthetic peptides derived from the PRXamide family members identified from the gray garden slug and insects (Table 1), were tested to determine their binding activities to two slug GPCRs (receptor A and B) expressed in the Sf9 insect cell line. All peptide ligands of SEQ ID NOs: 1-16 and 19-28, as well as the "RY" dipeptide and "PRY" tripeptide (purity >95%) were synthesized from Peptide 2.0 (Chantily, VA, USA). Sf9 cells were cultured as described previously (Choi et al., supra). About 50,000 cells per well in a 96-well plate (Corning C3603) were incubated at 28° C. overnight. At 48 h, cells were rinsed with 100 μL of fresh medium without fetal bovine serum (FBS). Then, cells were incubated in 95 μL of 1×FLIPR Calcium 6 reagent (Molecular Devices, San Jose, CA, USA) containing 2.5 mM probenecid at room temperature in the dark for 1 h. The reagent-loaded cells were transferred to the Flexstation 3 multimode microplate reader (Molecular Devices) equipped with filters (excitation: 485 nm and emission: 520 nm) and an 8-channel pipettor. Fluorescence measurements from each well on the column were taken every 5 s for 4 min. After 30 s the peptide ligand (10 μL) was added with the pipettor and fluorescent intensity was measured for up to 3 min. Then, 5 μL of 1 μM ionomycin (Thermo Fisher Scientific) was added to the cells to obtain a maximum fluorescence reading. Baseline fluorescence was determined by averaging 5 time points from each well prior to treatment with ligand and the resulting response was expressed as a percent increase in fluorescence relative to baseline value. Cells were tested only once with a ligand then discarded. Data were analyzed using Microsoft Excel as described previously, and half-maximal effective concentration ($EC_{50}$) values of ligands were determined using GraphPad Prism 6 (GraphPad Software, Inc., San Diego, CA).

Figure 2:
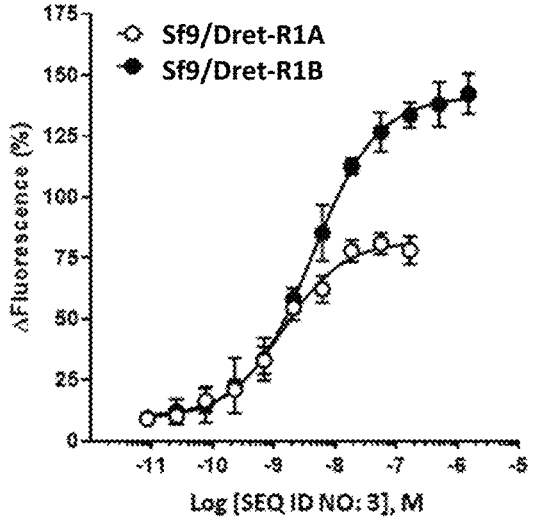
FIG. 2A and FIG. 2B provide a graphic representation of the dosage response of two peptides: SEQ ID NO: 3 (FIG. 2A) and SEQ ID NO: 4 (FIG. 2B) on two receptors (variant A or variant B.)

Results of the initial screening of each of the peptides on Sf9 cells, indicated that two of the peptides were the most likely candidates for additional analysis (FIG. 1). The binding affinity to the two receptors of these two peptides, QPPLPRY-$NH_2$ (SEQ ID NO: 3) and QPPVPRY-$NH_2$ (SEQ ID NO: 4), was measured based on specific fluorescent intensity of the Sf9 cells expressing receptor A or receptor B in a 96-well plate. A strong fluorescent signal indicated strong binding activity between the peptide ligand and receptor. The $EC_{50}$ values of SEQ ID NO: 3 (FIG. 2A) and SEQ ID NO: 4 (FIG. 2B) peptides were 1.4 and 12.7 nM, respectively, as determined with in vitro cell line experiments.

Example 2

Body Weight Loss Induced by Peptides

Figure 3:
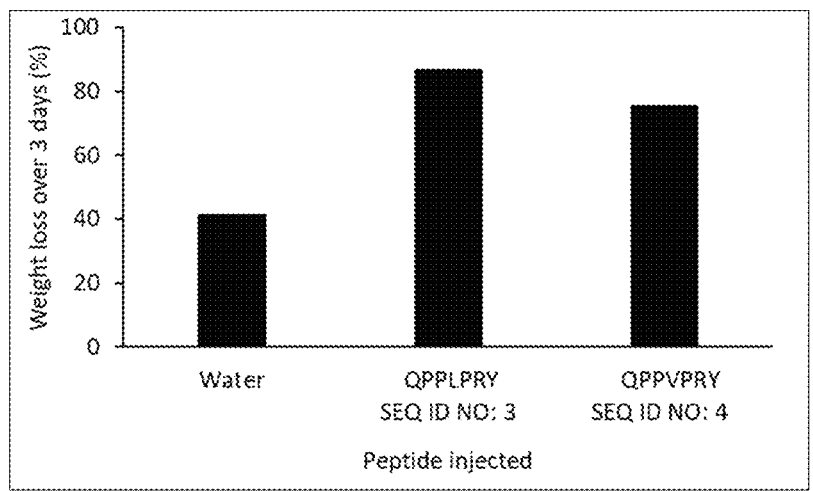
FIG. 3 provides a graphic representation of phenotypic effects of injection of molluscicidal peptides. Body weight loss induced by injecting gray garden slugs with water control (left column), SEQ ID NO: 3 (middle column), or SEQ ID NO: 4 (right column).
Figure 4:
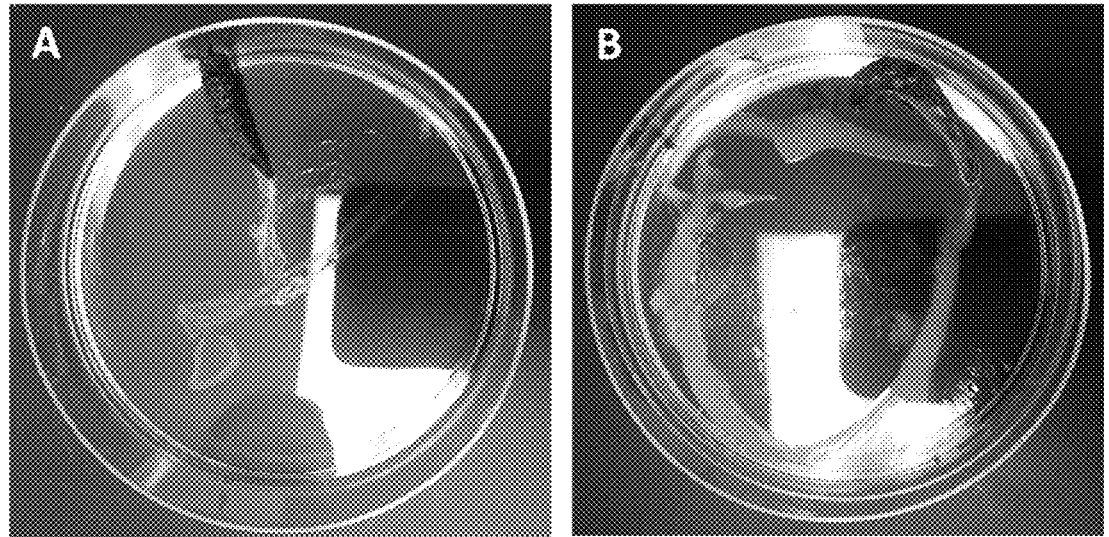
FIG. 4 provides a pictorial representation of altered mucus production in untreated (panel A) and treated (panel B) slugs. Slugs were injected with water only (panel A) or—SEQ ID NO: 3 (panel B).

To test their effects on slugs, peptides of SEQ ID NO: 3 and SEQ ID NO: 4 were dissolved in 5 μl of purified water (10 nmol) and injected into four gray garden slugs per each treatment. Over 80% of the slug body weight was lost after 72 h when either peptide was injected into the slugs, almost 2-fold higher than the water control (FIG. 3). Additionally, slugs injected with peptide (SEQ ID NO: 3) excreted large volumes of milky mucus within 1 minute, exhibited body paralysis, extruding tentacles, weight loss and dehydration (FIG. 4, exemplary results).

Example 3

Mortality Induced by Peptides

Figure 5:
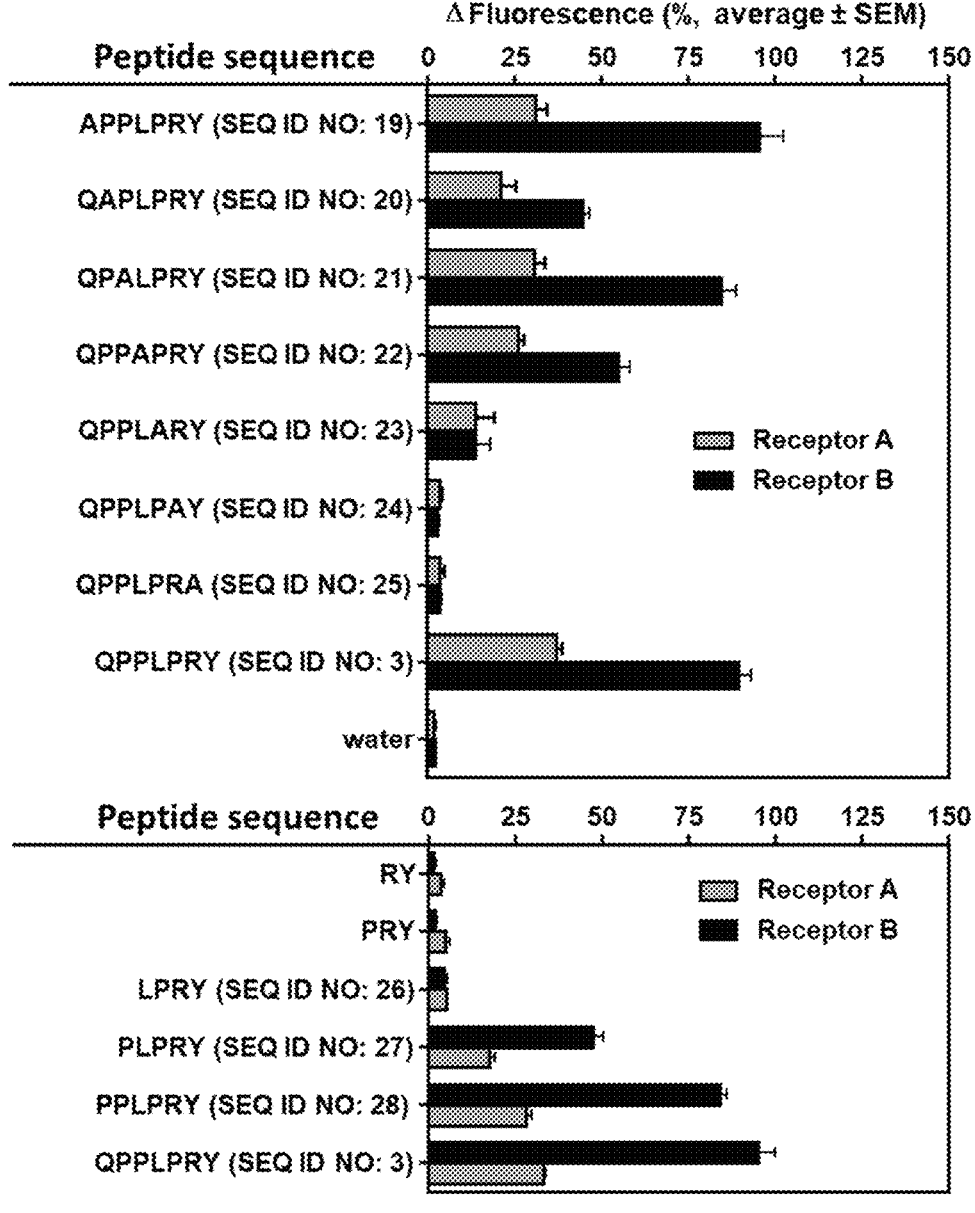
FIG. 5 provides a graphic representation of the dosage response of several synthetic peptides on two GPCRs (variant A or variant B.)

To test the effect of varying individual amino acid residues and varying the length of the peptide of SEQ ID NO: 3, different amino acid residues were replaced with alanine (A), or the overall length of the peptide was reduced by sequentially removing amino acid residues from the N-terminal end of SEQ ID NO: 3 (Table 1, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28). Altered peptides were tested and measured for binding activity with the receptors using the same methods as described above. Some altered peptides (SEQ ID NO: 19, SEQ ID NO: 20, SEQ ID NO: 21, SEQ ID NO: 22) maintained binding activity and activated the receptors (FIG. 5, exemplary results). Reduced peptides (SEQ ID NO: 26, SEQ ID NO: 27, SEQ ID NO: 28) also retained the ability to activate the receptors (FIG. 5, exemplary result). The results in these two case studies indicated that the RY and PRY sequences located at the C-termini of peptides may play a role in the binding activity of these peptides. These results suggest that similar small peptides also can be also modified and/or conjugated with other peptides or compounds to activate receptors.

Figure 6:
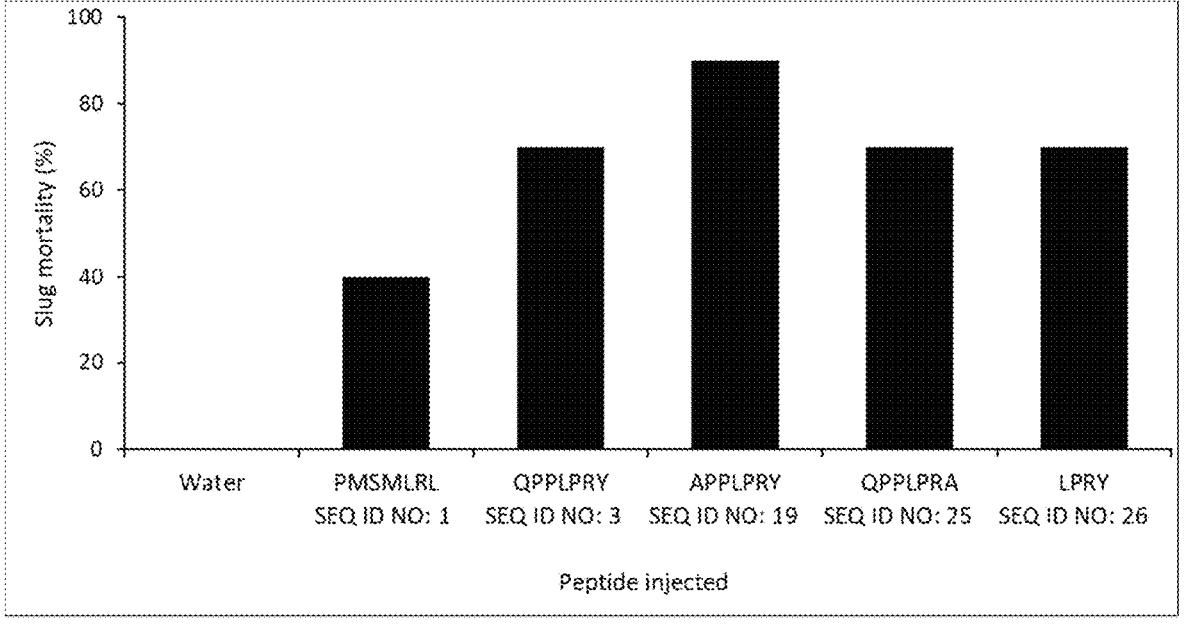
FIG. 6 and FIG. 7: provides a graphic representation of phenotypic effects of injection of molluscicidal peptides.
Figure 7:
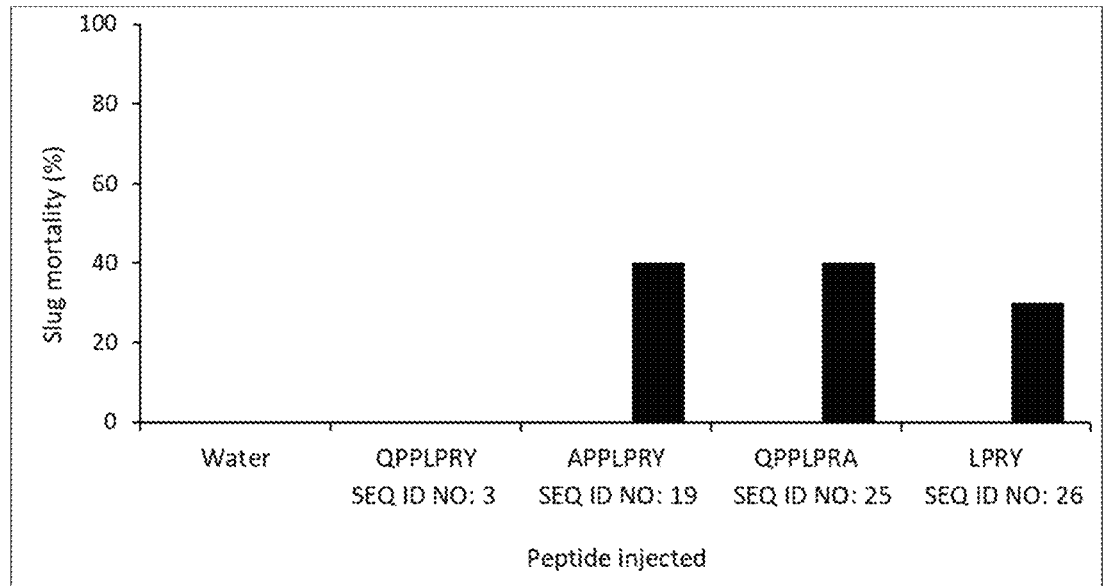

To test their effects on slugs, 100 nmol of each of the peptides (SEQ ID NO: 1, SEQ ID NO: 3, SEQ ID NO: 19, SEQ ID NO: 25 and SEQ ID NO: 26) was dissolved in 5 μL of purified water (100 nmol) and injected into 10 gray garden slugs per each treatment. Under dry conditions, after 24 h the slug mortalities observed were 40% with SEQ ID NO: 1, 70% with SEQ ID NO: 3, 90% with SEQ ID NO: 19, 70% with SEQ ID NO: 25, and 70% with SEQ ID NO: 26. However, no mortalities were observed in the control (water injected) slugs (FIG. 6, exemplary result). Under wet conditions, the slug mortalities observed within 24 h were 40% with SEQ ID NO: 19, 40% with SEQ ID NO: 25, and 30% with SEQ ID NO: 26. No mortalities were observed in the control (water injected) or in SEQ ID NO: 3 injected slugs (FIG. 7, exemplary result).

Example 4

Anti-Feeding Induced by Peptides

Figure 8:
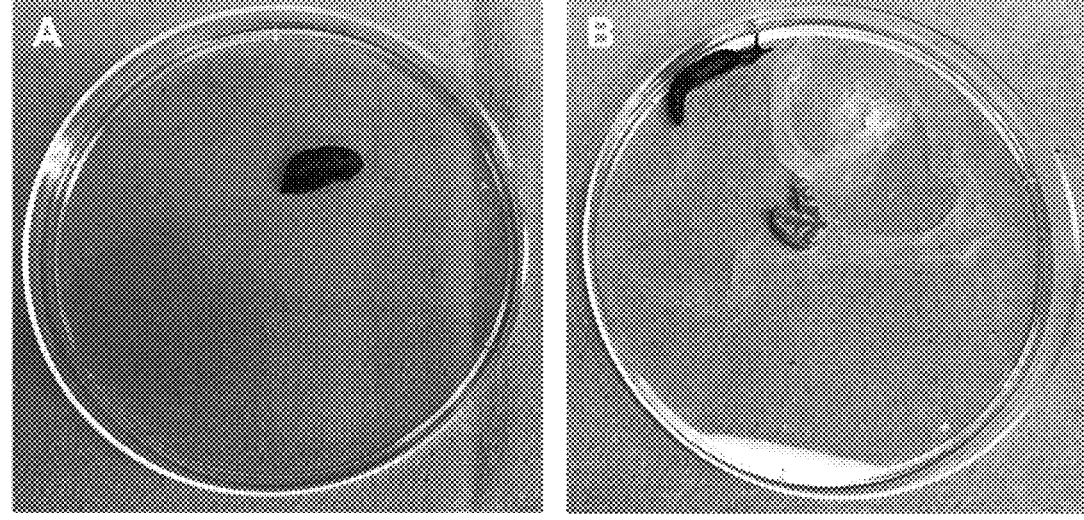
FIG. 8 provides a pictorial representation of altered mucus production in slugs fed on lettuce treated water only (panel A) and lettuce treated with SEQ ID NO: 3 (panel B).

To test for the effect of the peptides on feeding, slugs were fed a diet of lettuce leaf tissues treated with water alone or with 200 nmol of individual peptides (SEQ ID NO: 19, SEQ ID NO: 25, and SEQ ID NO: 26) dissolved in 10 μL water (FIG. 8). Ten gray garden slugs were used for each treatment and each treatment was replicated three times.

Figure 9A:
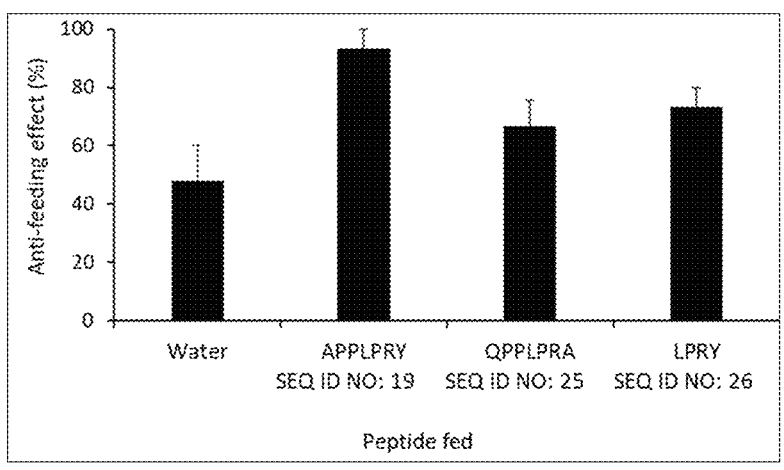
FIG. 9A, FIG. 9B and FIG. 9C provide a graphic representation of anti-feeding effects of peptides. Slugs were fed with lettuce treated with water or—lettuce treated with SEQ ID NO: 19, SEQ ID NO: 25, or SEQ ID NO: 26 and data was taken within 1 h (FIG. 9A), 2 h (FIG. 9B) or 6 h (FIG. 9C).
Figure 9B:
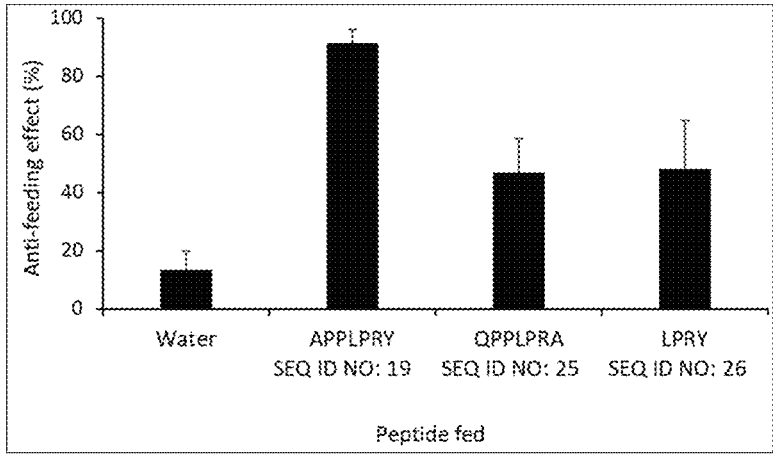
Figure 9C:
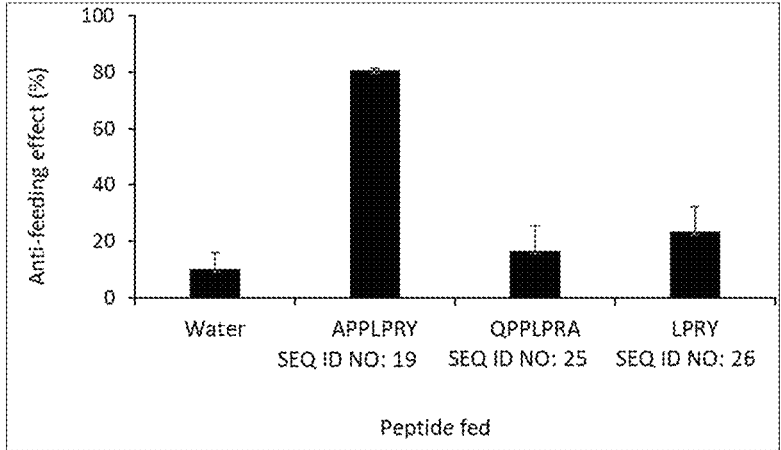

The maximum anti-feeding effect was observed with SEQ ID NO: 19. Anti-feeding was significantly ($p < 0.05$) increased at 93.3% within 1 h with SEQ ID NO: 19 compared to the water treatment (control) value of 48.0%. Peptides SEQ ID NO: 25 (66.7%) and SEQ ID NO: 26 (73.3%) did not show statistically significant anti-feeding effects (FIG. 9A, exemplary result). The maximum anti-feeding effect of SEQ ID NO: 19 on slugs was significantly ($p < 0.01$) increased at 91.3% within 2 h when compared to the water treatment (13.3%), but peptides SEQ ID NO: 25 (46.7%) and SEQ ID NO: 26 (48.0%) did not show statistically significant anti-feeding effects (FIG. 9B, exemplary result). The maximum anti-feeding effect of SEQ ID NO: 19 on the slugs was significantly ($p < 0.001$) increased at 80.7% within 6 h when compared to the water treatment (10.0%) and SEQ ID NO: 25 (16.7%), and significantly ($P < 0.01$)

increased when compared to SEQ ID NO: 26 (23.3%) (FIG. 9C, exemplary result).

While the invention has been described with reference to details of the illustrated embodiments, these details are not intended to limit the scope of the invention as defined in the appended claims. The embodiment of the invention in which exclusive property or privilege is claimed is defined as follows:

```
                            SEQUENCE LISTING

Sequence total quantity: 28
SEQ ID NO: 1             moltype = AA   length = 7
FEATURE                  Location/Qualifiers
REGION                   1..7
                         note = Chemically Synthesized
source                   1..7
                         mol_type = protein
                         organism = synthetic construct
SEQUENCE: 1
PMSMLRL                                                              7

SEQ ID NO: 2             moltype = AA   length = 8
FEATURE                  Location/Qualifiers
REGION                   1..8
                         note = Chemically Synthesized
source                   1..8
                         mol_type = protein
                         organism = synthetic construct
SEQUENCE: 2
GQFSAARL                                                             8

SEQ ID NO: 3             moltype = AA   length = 7
FEATURE                  Location/Qualifiers
REGION                   1..7
                         note = Chemically Synthesized
source                   1..7
                         mol_type = protein
                         organism = synthetic construct
SEQUENCE: 3
QPPLPRY                                                              7

SEQ ID NO: 4             moltype = AA   length = 7
FEATURE                  Location/Qualifiers
REGION                   1..7
                         note = Chemically Synthesized
source                   1..7
                         mol_type = protein
                         organism = synthetic construct
SEQUENCE: 4
QPPVPRY                                                              7

SEQ ID NO: 5             moltype = AA   length = 9
FEATURE                  Location/Qualifiers
REGION                   1..9
                         note = Chemically Synthesized
source                   1..9
                         mol_type = protein
                         organism = synthetic construct
SEQUENCE: 5
FFFRPAPRG                                                            9

SEQ ID NO: 6             moltype = AA   length = 14
FEATURE                  Location/Qualifiers
REGION                   1..14
                         note = Chemically Synthesized
source                   1..14
                         mol_type = protein
                         organism = synthetic construct
SEQUENCE: 6
VFYTKSDDND YPRI                                                      14

SEQ ID NO: 7             moltype = AA   length = 14
FEATURE                  Location/Qualifiers
REGION                   1..14
                         note = Chemically Synthesized
source                   1..14
                         mol_type = protein
                         organism = synthetic construct
SEQUENCE: 7
GIFTQSAHGY SPRV                                                      14
```

-continued

```
SEQ ID NO: 8          moltype = AA   length = 9
FEATURE               Location/Qualifiers
REGION                1..9
                      note = Chemically Synthesized
source                1..9
                      mol_type = protein
                      organism = synthetic construct
SEQUENCE: 8
SGYLAFPRM                                                      9

SEQ ID NO: 9          moltype = AA   length = 15
FEATURE               Location/Qualifiers
REGION                1..15
                      note = Chemically Synthesized
source                1..15
                      mol_type = protein
                      organism = synthetic construct
SEQUENCE: 9
TGPSASSGLW FGPRL                                               15

SEQ ID NO: 10         moltype = AA   length = 8
FEATURE               Location/Qualifiers
REGION                1..8
                      note = Chemically Synthesized
source                1..8
                      mol_type = protein
                      organism = synthetic construct
SEQUENCE: 10
SVPFKPRL                                                       8

SEQ ID NO: 11         moltype = AA   length = 18
FEATURE               Location/Qualifiers
REGION                1..18
                      note = Chemically Synthesized
source                1..18
                      mol_type = protein
                      organism = synthetic construct
SEQUENCE: 11
DDSSPGFFLK ITKNVPRL                                            18

SEQ ID NO: 12         moltype = AA   length = 33
FEATURE               Location/Qualifiers
REGION                1..33
                      note = Chemically Synthesized
source                1..33
                      mol_type = protein
                      organism = synthetic construct
SEQUENCE: 12
LSDDMPATPA DQEMYRQDPE QIDSRTKYFS PRL                           33

SEQ ID NO: 13         moltype = AA   length = 9
FEATURE               Location/Qualifiers
REGION                1..9
                      note = Chemically Synthesized
source                1..9
                      mol_type = protein
                      organism = synthetic construct
SEQUENCE: 13
FYAPFSPRL                                                      9

SEQ ID NO: 14         moltype = AA   length = 10
FEATURE               Location/Qualifiers
REGION                1..10
                      note = Chemically Synthesized
source                1..10
                      mol_type = protein
                      organism = synthetic construct
SEQUENCE: 14
DAGLFPFPRV                                                     10

SEQ ID NO: 15         moltype = AA   length = 9
FEATURE               Location/Qualifiers
REGION                1..9
                      note = Chemically Synthesized
source                1..9
                      mol_type = protein
                      organism = synthetic construct
SEQUENCE: 15
EQLIPFPRV                                                      9
```

```
SEQ ID NO: 16          moltype = AA   length = 15
FEATURE                Location/Qualifiers
REGION                 1..15
                       note = Chemically Synthesized
source                 1..15
                       mol_type = protein
                       organism = synthetic construct
SEQUENCE: 16
NGASGNGGLW FGPRL                                                        15

SEQ ID NO: 17          moltype = AA   length = 7
FEATURE                Location/Qualifiers
REGION                 1..7
                       note = Chemically Synthesized
SITE                   4
                       note = misc_feature - Xaa can be any naturally occurring
                        amino acid
source                 1..7
                       mol_type = protein
                       organism = synthetic construct
SEQUENCE: 17
QPPXPRY                                                                 7

SEQ ID NO: 18          moltype =    length =
SEQUENCE: 18
000

SEQ ID NO: 19          moltype = AA   length = 7
FEATURE                Location/Qualifiers
REGION                 1..7
                       note = Chemically Synthesized
source                 1..7
                       mol_type = protein
                       organism = synthetic construct
SEQUENCE: 19
APPLPRY                                                                 7

SEQ ID NO: 20          moltype = AA   length = 7
FEATURE                Location/Qualifiers
REGION                 1..7
                       note = Chemically Synthesized
source                 1..7
                       mol_type = protein
                       organism = synthetic construct
SEQUENCE: 20
QAPLPRY                                                                 7

SEQ ID NO: 21          moltype = AA   length = 7
FEATURE                Location/Qualifiers
REGION                 1..7
                       note = Chemically Synthesized
source                 1..7
                       mol_type = protein
                       organism = synthetic construct
SEQUENCE: 21
QPALPRY                                                                 7

SEQ ID NO: 22          moltype = AA   length = 7
FEATURE                Location/Qualifiers
REGION                 1..7
                       note = Chemically Synthesized
source                 1..7
                       mol_type = protein
                       organism = synthetic construct
SEQUENCE: 22
QPPAPRY                                                                 7

SEQ ID NO: 23          moltype = AA   length = 7
FEATURE                Location/Qualifiers
REGION                 1..7
                       note = Chemically Synthesized
source                 1..7
                       mol_type = protein
                       organism = synthetic construct
SEQUENCE: 23
QPPLARY                                                                 7

SEQ ID NO: 24          moltype = AA   length = 7
```

-continued

```
FEATURE            Location/Qualifiers
REGION             1..7
                   note = Chemically Synthesized
source             1..7
                   mol_type = protein
                   organism = synthetic construct
SEQUENCE: 24
QPPLPAY                                                    7

SEQ ID NO: 25      moltype = AA   length = 7
FEATURE            Location/Qualifiers
REGION             1..7
                   note = Chemically Synthesized
source             1..7
                   mol_type = protein
                   organism = synthetic construct
SEQUENCE: 25
QPPLPRA                                                    7

SEQ ID NO: 26      moltype = AA   length = 4
FEATURE            Location/Qualifiers
REGION             1..4
                   note = Chemically Synthesized
source             1..4
                   mol_type = protein
                   organism = synthetic construct
SEQUENCE: 26
LPRY                                                       4

SEQ ID NO: 27      moltype = AA   length = 6
FEATURE            Location/Qualifiers
REGION             1..6
                   note = Chemically Synthesized
source             1..6
                   mol_type = protein
                   organism = synthetic construct
SEQUENCE: 27
PPLPRY                                                     6

SEQ ID NO: 28      moltype = AA   length = 5
FEATURE            Location/Qualifiers
REGION             1..5
                   note = Chemically Synthesized
source             1..5
                   mol_type = protein
                   organism = synthetic construct
SEQUENCE: 28
PLPRY                                                      5
```

What is claimed is:

1. A composition comprising an isolated synthetic peptide having SEQ ID NO: 19, SEQ ID NO: 20, SEQ ID NO: 21, SEQ ID NO: 22, SEQ ID NO: 25, SEQ ID NO: 26, SEQ ID NO: 27, SEQ ID NO: 28, or a combination thereof in an aqueous solution at a concentration of at least 10 nmol, and further comprising a slug food material, and a phagostimulant.

2. The composition of claim 1, comprising SEQ ID NO: 19.

3. The composition of claim 1, comprising SEQ ID NO: 20.

4. The composition of claim 1, comprising SEQ ID NO: 21.

5. The composition of claim 1, comprising SEQ ID NO: 22.

6. The composition of claim 1, comprising SEQ ID NO: 25.

7. The composition of claim 1, comprising SEQ ID NO: 26.

8. The composition of claim 1, comprising SEQ ID NO: 27.

9. The composition of claim 1, comprising SEQ ID NO: 28.

10. A molluscicide composition for controlling a slug, the composition comprising an effective amount of a synthetic peptide having SEQ ID NO: 19, SEQ ID NO: 20, SEQ ID NO: 21, SEQ ID NO: 22, SEQ ID NO: 25, SEQ ID NO: 26, SEQ ID NO: 27, SEQ ID NO: 28, or a combination thereof in an aqueous solution at a concentration of at least 10 nmol and further comprising a slug food material, and a phagostimulant.

11. The molluscicide of claim 10, comprising SEQ ID NO: 19.

12. The molluscicide of claim 10, comprising SEQ ID NO: 20.

13. The molluscicide of claim 10, comprising SEQ ID NO: 21.

14. The molluscicide of claim 10, comprising SEQ ID NO: 22.

15. The molluscicide of claim 10, comprising SEQ ID NO: 25.

16. The molluscicide of claim 10, comprising SEQ ID NO: 26.

17. The molluscicide of claim 10, comprising SEQ ID NO: 27.

18. The molluscicide of claim 10, comprising SEQ ID NO: 28.

19. A method for controlling a slug comprising contacting a slug or its environment with a biologically effective amount of a compound of claim 1, or a molluscicide of claim 10 wherein the mortality of said slug increases.

20. The method of claim 19, wherein the slug is *Deroceras reticulatum*.

\*  \*  \*  \*  \*